United States Patent [19]

Asgar et al.

[11] 4,374,085

[45] Feb. 15, 1983

[54] SILVER-TIN-COPPER-PALLADIUM ALLOY AND AMALGAM THEREOF

[75] Inventors: Kamal Asgar, Ann Arbor, Mich.; Steven H. Reichman, New Hartford, N.Y.

[73] Assignee: Special Metals Corporation, New Hartford, N.Y.

[21] Appl. No.: 154,200

[22] Filed: May 29, 1980

[51] Int. Cl.³ .................. C22C 9/00; C22C 30/02
[52] U.S. Cl. .................... 420/470; 420/471; 420/473; 420/476; 420/503; 420/527; 420/587
[58] Field of Search .......... 75/173 C, 169, 134 B, 75/134 C, 154, 157

[56] References Cited

U.S. PATENT DOCUMENTS 3,676,112  7/1972  Muhler .................. 75/173 C
3,871,876  3/1975  Asgar et al. .............. 75/169
3,975,192  8/1976  Simpson ................. 75/169

FOREIGN PATENT DOCUMENTS 1032272  6/1966  United Kingdom.

OTHER PUBLICATIONS

Nakamura et al., Cellular Responses to the Dispersion Amalgams in Vitro, Journal of Dental Research, vol. 58, No. 8, Aug. 1979, pp. 1780–1790.
Eames et al., Eight High–Copper Amalgam Alloys and Six Conventional Alloys Compared, Operative Density, vol. 1, No. 3, Summer, 1976.

*Primary Examiner*—R. Dean
*Attorney, Agent, or Firm*—James C. Valentine; John K. Williamson

[57] ABSTRACT

A silver-tin-copper-palladium alloy containing from 30 to 70% silver, 15 to 37% tin, at least 13% copper and from 0.05 to 0.95% palladium; and an amalgam thereof.

20 Claims, No Drawings

SILVER-TIN-COPPER-PALLADIUM ALLOY AND AMALGAM THEREOF

The present invention relates to an alloy, and in particular, an amalgamable dental alloy; and to an amalgam formed therefrom.

Dental amalgams are prepared in dental offices by reacting amalgamable powder alloys with mercury. One such alloy is comprised of silver and tin. The reaction products are silver-mercury, tin-mercury and some unreacted silver-tin powder, respectively known to those skilled in the art as $\gamma_1$, $\gamma_2$, and $\gamma$ phases. Tin-mercury ($\gamma_2$) is the weakest and least corrosion resistant of these phases.

Various measures are taken to reduce or eliminate $\gamma_2$ in dental amalgams. One means involves the mixing of silver-copper eutectic powder with conventional silver-tin powder. Another involves the addition of copper thereto. These measures are discussed in the following references: "Eight High-copper Amalgam Alloys and Six Conventional Alloys Compared", W. B. Eames and J. F. MacNamara, Operative Density—Volume 1, No. 3, Summer, 1976; "Relationship Between Microstructure, Creep, And Strength In Dental Amalgam", Manohar L. Malhotra and Kamal Asgar, presented in 1977 at the Annual Meeting of the International Association for Dental Research; U.S. Pat. No. 3,871,876; and U.S. Pat. No. 3,975,192.

Although copper additions to silver-tin alloys have eliminated or reduced $\gamma_2$, disadvantages are associated therewith. Oxidation which adversely affects the handling characteristics of such alloys, has been detected prior to amalgamation. There is also a tendency for restorations filled with amalgams formed from such alloys to darken and tarnish after a relatively short period.

Through the present invention, there is provided an alloy which overcomes the disadvantages of copper additions. Small amounts of palladium are added to silver-tin-copper alloys, thereby increasing their nobility. Palladium is added in amounts of from 0.05 to 0.95%. Larger amounts have been found to significantly increase the cost of the alloy, with only minimal, if any, further increases in corrosion resistance.

No mention of palladium is found in any of the references referred to hereinabove. Reference to palladium is, however, found in U.S. Pat. No. 3,676,112 and in an article entitled, "Cellular Responses to the Dispersion Amalgams in vitro", by M. Nakamura and H. Kawahara. The article appeared in the August 1979 issue of the Journal of Dental Research, pages 1780–1790, Vol. 58, No. 8. U.S. Pat. No. 3,676,112 deals with the addition of stannous hexafluorozirconate to dissimilar alloys. It does not attribute any benefit to palladium and does not disclose a single palladium-bearing example. The article refers to an alloy having a palladium content in excess of that for the subject invention. Also, United Kingdom Pat. No. 1,032,272 discloses the use of from 0.001 to 19.9% of either palladium or platinum in a high silver content, specifically from 80 to 99.5% silver, pulverulent silver alloy. It is noted that such alloy has a total copper plus tin content of, at most, 6%.

It is accordingly an object of the present invention to provide an alloy, and in particular, an amalgamable dental alloy; and an amalgam formed therefrom.

The alloy of the subject invention consists essentially of, by weight, 30 to 65% silver, 15 to 37% tin, 0.05 to 0.95% palladium, up to 4% zinc, up to 6% indium, up to 5% manganese, up to 2% cadmium, up to 2% aluminum, up to 5% gallium, up to 2% ruthenium, up to 3% mercury, balance essentially copper. Copper is present in amounts of at least 13%.

Copper is usually present in amounts of at least (8) 13% and preferably in amounts of at least (13) 20%, for its effect in eliminating or reducing the detrimental gamma 2 phase. Silver and tin are usually present within respective ranges of 30 to 60 and 20 to 35%. Preferred silver and tin ranges are respectively 30 to 55 and 25 to 32%. Palladium is usually present in amounts of from 0.01 to 0.9%, and preferably in amounts of from 0.2 to 0.8%. The various ranges for the referred to elements have both an individual and synergistic affect upon the alloy, thereby representing many embodiments thereof. Optional additions are seldom present in amounts greater than 5%. The alloy is not dependent upon any additions other than silver, tin, copper and palladium, and usually contains at least 95% of these elements. Additions such as indium can darken the alloy. The alloy is usually present as an atomized powder.

Palladium is added to the subject alloy to improve its corrosion resistance. Oxidation which adversely affects the handling characteristics of the alloy prior to amalgamation, is not evident once palladium is added thereto. Similarly, with palladium, the tendency of restoration fillings to darken and tarnish after a relatively short period is overcome.

In addition to increasing the nobility of the alloy, palladium has been shown to reduce creep under a given load and temperature. Alloys possessing lower creep values generally behave better in the mouth.

The amalgam of the subject invention is formed by triturating from 30 to 56% of mercury with from 44 to 70% of the subject dental alloy. Triturating is performed in accordance with procedures well known to those skilled in the art. Mercury is usually present in amounts of from 37 to 48%.

The following examples are illustrative of several embodiments of the invention.

Six alloys (Alloys A through F) were atomized and amalgamated. The composition of the alloys appears hereinbelow in Table I.

TABLE I

| Alloy | COMPOSITION (wt. %) | | | | |
|---|---|---|---|---|---|
| | Ag | Sn | Cu | Pd | Ru |
| A. | 50 | 30 | 20 | — | — |
| B. | 49.8 | 30 | 20 | 0.2 | — |
| C. | 49.2 | 30 | 20 | 0.2 | 0.5 |
| D. | 49.5 | 30 | 20 | 0.5 | — |
| E. | 50 | 28.75 | 20 | 1.25 | — |
| F. | 48.5 | 30 | 20 | 1.5 | — |

The physical properties, namely the compressive strength, of amalgams of the above alloys which contained from 40 to 43.8% mercury are set forth in Table II. It is noted that creep statistics (see Table IV) and compressive strength statistics, below, are considered to be a comparable indication of the clinical behavior of dental alloys.

TABLE II

| Alloy | Compressive Strength (1,000 psi) | |
|---|---|---|
| | 1 hour | 1 day |
| A. | 34.5 | 53.4 |
| B. | 41 | 66 |
| C. | 40 | 67 |
| D. | 47.5 | 75 |
| E. | 40 | 70 |
| F. | 48.5 | 73.4 |

An electropotential study was conducted to study the corrosion resistance of the amalgams which contained from 40 to 43.8% mercury. Under a given potential (voltage) the higher the current carried by an amalgam, the faster it will corrode. Results of a 24 hour test for each amalgam, appear hereinbelow in Table III.

TABLE III

| AMALGAM | INTEGRATED ANODIC CURRENT DENSITY (AMPERES/SQUARE CENTIMETER) AT 0.0V (SCE) IN ONE % NaCl AT 37° C. |
|---|---|
| A. | 10.3 |
| B. | 5.4 |
| C. | 5.4 |
| D. | 2.5 |
| E. | 1.7 |
| F. | 2.2 |

Note the lower current carried by the palladium-bearing amalgams (B-F) as contrasted to the palladium-free amalgam (A), and accordingly, the superior corrosion resistance thereof. A logarithmic plot of these values shows that the corrosion resistance peaks at a palladium content of about 0.95% and then proceeds to decrease with increasing levels thereof.

Additional specimens of amalgams A-F were tested to determine their creep characteristics. The specimens were tested after aging for seven days, under a compressive load of approximately 5,000 psi and at a temperature of 37° C. (body temperature). Testing was for a period of 4 hours, with changes during the first hour being disregarded. The percent reduction in height of the specimens is reported hereinbelow in Table IV.

TABLE IV

| AMALGAM | PERCENT REDUCTION |
|---|---|
| A. | 0.4 |
| B. | 0.14 |
| C. | 0.15 |
| D. | 0.2 |
| E. | 0.04 |
| F. | 0.08 |

Note that the percent reductions for Amalgams B-F are substantially lower than that for Alloy A. As noted hereinabove, Amalgams B-F are palladium bearing, whereas Amalgam A is not. Amalgam A was formed from an alloy devoid of palladium.

It will be apparent to those skilled in the art that the novel principle of the invention disclosed herein in connection with specific examples thereof will suggest various other modifications and applications of the same. It is accordingly desired that in construing the breadth of the appended claims they shall not be limited to the specific examples of the invention described herein.

I claim:

1. An amalgable dental alloy consisting essentially of, by weight, 30 to 70% silver, 15 to 37% tin, 0.05 to 0.95% palladium, up to 4% zinc, up to 6% indium, up to 5% manganese, up to 2% cadmium, up to 2% aluminum, up to 5% gallium, up to 2% ruthenium, up to 3% mercury, balance essentially copper; said alloy having at least 13% copper and no tin-mercury phase after trituration with mercury.

2. An alloy according to claim 1, having 0.1 to 0.9% palladium.

3. An alloy according to claim 2, having 0.2 to 0.8% palladium.

4. An alloy according to claim 1, having at least about 20% copper.

5. An alloy according to claim 4, having about 0.5% palladium.

6. An alloy according to claim 1, consisting essentially of, by weight, 30 to 60% silver, 20 to 35% tin, 0.1 to 0.9% palladium, up to 4% zinc, up to 6% indium, up to 5% manganese, up to 2% cadmium, up to 2% aluminum, up to 5% gallium, up to 2% ruthenium, up to 3% mercury, balance essentially copper; said alloy having at least 13% copper.

7. An alloy according to claim 6, having 0.2 to 0.8% palladium.

8. An alloy according to claim 6, having at least about 20% copper.

9. An alloy according to claim 1, having a silver plus tin plus palladium plus copper content of at least 95%.

10. An alloy according to claim 1, consisting essentially of, by weight, 40 to 55% silver, 25 to 32% tin, 0.2 to 0.8% palladium, balance essentially copper; said alloy having at least 13% copper.

11. An amalgam formed from 30 to 56% of mercury and 44 to 70% of a dental alloy; said dental alloy consisting essentially of, by weight, 30 to 70% silver, 15 to 37% tin, 0.05 to 0.95% palladium, up to 4% zinc, up to 6% indium, up to 5% manganese, up to 2% cadmium, up to 2% aluminum, up to 5% gallium, up to 2% ruthenium, up to 3% mercury, balance essentially copper; said dental alloy having at least 13% copper and said amalgam being free of a tin-mercury phase.

12. An amalgam according to claim 11, wherein said dental alloy has 0.01 to 0.9% palladium.

13. An amalgam according to claim 12, wherein said dental alloy has 0.2 to 0.8% palladium.

14. An amalgam according to claim 11, wherein said dental alloy has at least about 20% copper.

15. An amalgam according to claim 14, wherein said dental alloy has about 0.5% palladium.

16. An amalgam according to claim 11, wherein said dental alloy consists essentially of, by weight, 30 to 60% silver, 20 to 35% tin, 0.1 to 0.9% palladium, up to 4% zinc, up to 6% indium, up to 5% manganese, up to 2% cadmium, up to 2% aluminum, up to 5% gallium, up to 2% ruthenium, up to 3% mercury, balance essentially copper; said dental alloy having at least 13% copper.

17. An amalgam according to claim 16, wherein said dental alloy has 0.2 to 0.8% palladium.

18. An amalgam according to claim 16, wherein said dental alloy has at least about 20% copper.

19. An amalgam according to claim 11, wherein said dental alloy has a silver plus tin plus palladium plus copper content of at least 95%.

20. An amalgam according to claim 11, wherein said dental alloy consists essentially of, by weight, 40 to 55% silver, 25 to 32% tin, 0.2 to 0.8% palladium, balance essentially copper; said dental alloy having at least 13% copper.

* * * * *